(12) United States Patent
Georgiev et al.

(10) Patent No.: US 9,549,687 B2
(45) Date of Patent: Jan. 24, 2017

(54) PATIENT TRANSPORT APPARATUS WITH INTEGRATED SUBSYSTEMS FOR USE IN MAGNETIC RESONANCE IMAGING

(75) Inventors: Emil Markov Georgiev, Hartland, WI (US); Jason A. Polzin, Lake Mills, WI (US); Ryan W. Rindy, McFarland, WI (US); Mark J. Stefka, Mukwonago, WI (US); Robert Meurer, Waukesha, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1788 days.

(21) Appl. No.: 12/188,251

(22) Filed: Aug. 8, 2008

(65) Prior Publication Data

US 2010/0031443 A1 Feb. 11, 2010

(51) Int. Cl.
*A61B 5/05* (2006.01)
*A61B 5/055* (2006.01)
*A61G 13/06* (2006.01)
*A61G 13/10* (2006.01)

(52) U.S. Cl.
CPC ............ *A61B 5/0555* (2013.01); *A61G 13/06* (2013.01); *A61G 13/107* (2013.01); *A61G 2210/50* (2013.01); *Y10T 29/49826* (2015.01)

(58) Field of Classification Search
USPC ......................... 600/410, 409, 415
See application file for complete search history.

(56) References Cited

U.S. PATENT DOCUMENTS

| | | | |
|---|---|---|---|
| 4,567,894 A | 2/1986 | Bergman | |
| 5,375,604 A | 12/1994 | Kelly et al. | |
| 5,626,151 A | 5/1997 | Linden | |
| 6,175,977 B1* | 1/2001 | Schumacher et al. | ............ 5/626 |
| 6,571,792 B1 | 6/2003 | Hendrickson et al. | |
| 6,899,103 B1 | 5/2005 | Hood et al. | |
| 2002/0038392 A1* | 3/2002 | De La Huerga | .................. 710/8 |
| 2002/0123682 A1* | 9/2002 | Allred et al. | ................. 600/411 |
| 2003/0069493 A1* | 4/2003 | Pan et al. | ...................... 600/410 |
| 2004/0103899 A1* | 6/2004 | Noble | ...................... 128/207.18 |
| 2005/0113668 A1* | 5/2005 | Srinivasan | .................... 600/411 |
| 2005/0277096 A1* | 12/2005 | Hendrickson et al. | ........ 434/262 |
| 2007/0124858 A1* | 6/2007 | Ahlman | ........................ 5/81.1 R |
| 2009/0036764 A1* | 2/2009 | Rivas et al. | .................. 600/365 |

* cited by examiner

*Primary Examiner* — Joel F Brutus (57) ABSTRACT

A patient transport apparatus having a table configured to support a patient, a base attached to the table, a docking system attached to the base, the docking system configured to couple to a mating docking system of an MR imaging system, and a plurality of bays formed in the base, with each bay configured to receive a patient care module therein. The patient transport apparatus further includes a control system configured to be electrically coupled to each patient care module received within the plurality of bays and configured to centrally control each patient care module.

19 Claims, 5 Drawing Sheets

PATIENT TRANSPORT APPARATUS WITH INTEGRATED SUBSYSTEMS FOR USE IN MAGNETIC RESONANCE IMAGING

BACKGROUND OF THE INVENTION

The invention relates generally to an apparatus useful in magnetic resonance (MR) imaging and, more particularly, to a table for transporting a patient from a preparation room to an MR examination room. In the MR examination room, the table can be used to position the patient within and retrieve the patient from, the bore of the MR imaging system.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Due to the nature of some MR scans, there is a patient population (e.g., children age 7 and below, claustrophobic patients, patients with Parkinsons'Disease, some elderly patients, etc.) that can benefit from anesthesia and other support systems to assist the patients to remain stationary for long periods of time throughout the MR scans. Generally, anesthesia systems include various pieces of equipment to anesthetize the patient, support or control respiration, and keep the patient in that state until some medical procedure is completed.

Anesthesia systems generally comprise a plurality of pressure regulators, vaporizers, gas mixing devices and flow control devices. The vaporizer converts a liquid anesthetic to gaseous form. The gas is then combined with life support gases and delivered to the patient, usually through a facemask or similar device. The anesthesia machine also handles various monitoring functions and gas supplies depending on the breathing circuit being used. The patient breathing circuit conveys the anesthetic (in gaseous form) to the patient and typically has an inspiratory limb tube through which gases are delivered to the patient and an expiratory limb tube through which exhaled gases are taken from the patient.

The time needed to set up and tear down the anesthesia and other support equipment can add as much as 30 to 40 minutes to MR exam times. Equipment contributing to the setup and tear-down processes may be, for example, an anesthesia machine, an IV pump, and a monitoring module, all of which need to be connected to the patient via associated hardware such as breathing tubes, IV lines, and monitoring cables. Typically these various cables, lines, and tubes lie on the floor near the table where they are susceptible to damage from traffic such as a mobile patient table, medical personnel, or the like. In cases where the setup and tear-down occur outside of the MR examination room, the separate equipment including the cables, lines, and tubes must be moved in and out of the MR examination room, which increases the chances for damaging the cables, lines, and tubes and may require extra personnel to transport the various support equipment and associated hardware to and from the MR examination room.

It would therefore be desirable to have a patient transport apparatus capable of transporting an anesthetized patient and support equipment to and from an MR examination room that reduces opportunities for equipment damage and simplifies transportation of the anesthetized patient and support equipment.

BRIEF DESCRIPTION OF THE INVENTION

In an aspect of the invention, a patient transport apparatus having a table configured to support a patient, a base attached to the table, a docking system attached to the base, the docking system configured to couple to a mating docking system of an MR imaging system, and a plurality of bays formed in the base, with each bay configured to receive a patient care module therein. The patient transport apparatus further includes a control system configured to be electrically coupled to each patient care module received within the plurality of bays and configured to centrally control each patient care module.

According to another aspect of the invention, a patient imaging system including a magnetic resonance imaging (MRI) system having a plurality of gradient coils positioned about a bore of a magnet, and an RF transceiver system and an RF switch controlled by a pulse module to transmit RF signals to an RF coil assembly to acquire MR images. The patient imaging system further includes a plurality of patient care modules configured to provide patient care during an imaging session and a patient transport apparatus, wherein the transport apparatus comprises a table configured to support a patient and a base attached to the table. The base includes a plurality of compartments having the plurality of modules positioned therein, a controller configured to control each of the plurality of modules, and a docking system configured to removeably attach the patient transport apparatus to the MRI system.

In yet another aspect of the invention, a method of manufacturing a patient transport apparatus that includes coupling a table for supporting a patient to a base, forming a plurality of compartments in the base capable of accepting a plurality of patient care modules therein, attaching a docking mechanism to the base, wherein the docking mechanism is capable of coupling the patient transport apparatus to an MRI system magnet, and providing a controller capable of controlling each of the plurality of patient care modules.

Various other features and advantages will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION OF THE PREFERRED EMBODIMENT

Figure 1:
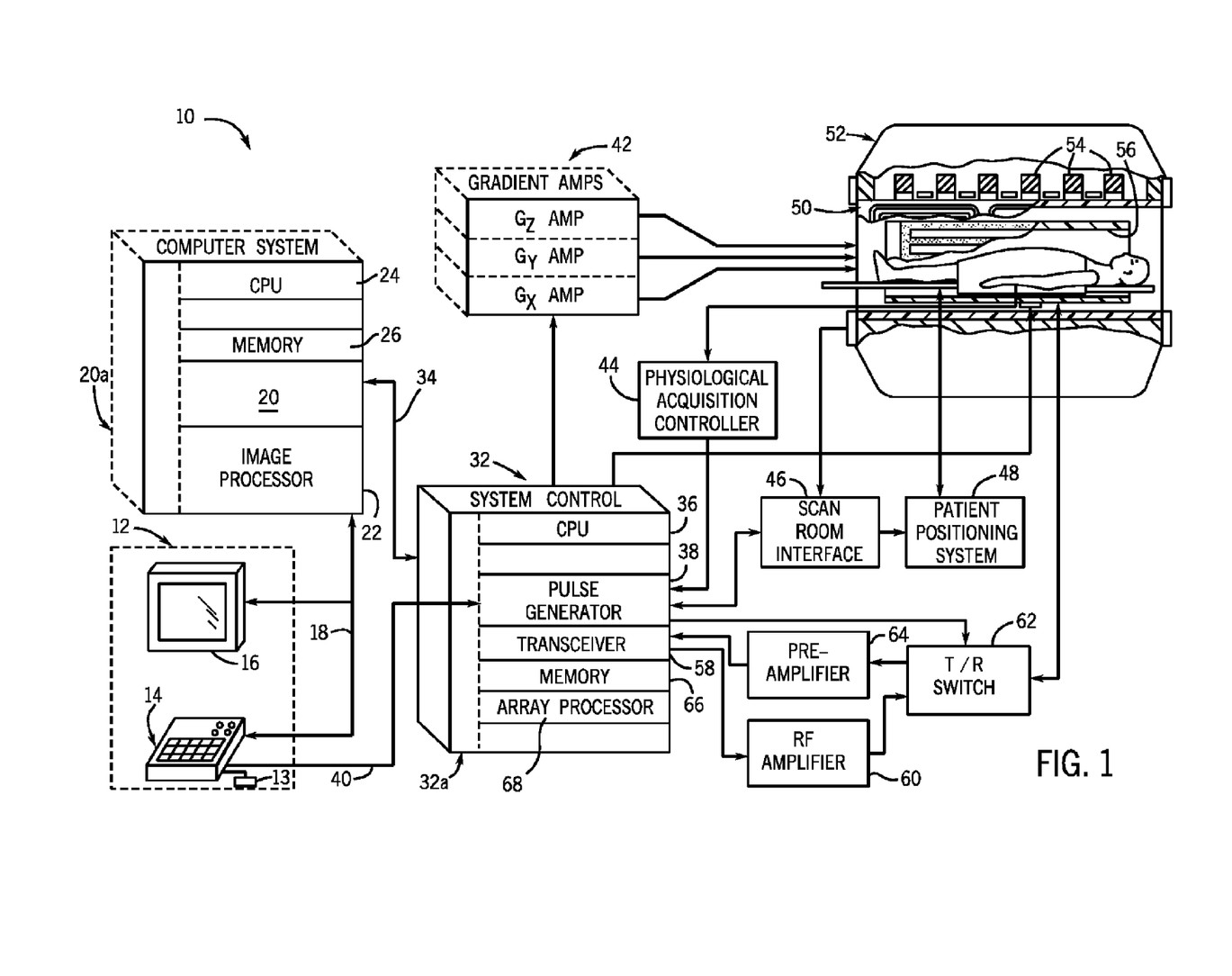
FIG. 1 is a schematic block diagram of an exemplary MR imaging system for use with embodiments of the invention.

Referring to FIG. 1, the major components of a preferred magnetic resonance imaging (MRI) system 10 incorporating an embodiment of the invention are shown. The operation of the system is controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20a. These include an image processor module 22, a CPU module 24 and a memory module 26 which may be a frame buffer for storing image data arrays. The computer system 20 communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having Gx, Gy, and Gz amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either the transmit or receive mode.

The MR signals picked up by the RF coil 56 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory. In response to commands received from the operator console 12, this image data may be archived in long term storage or it may be further processed by the image processor 22 and conveyed to the operator console 12 and presented on the display 16.

Figure 2:
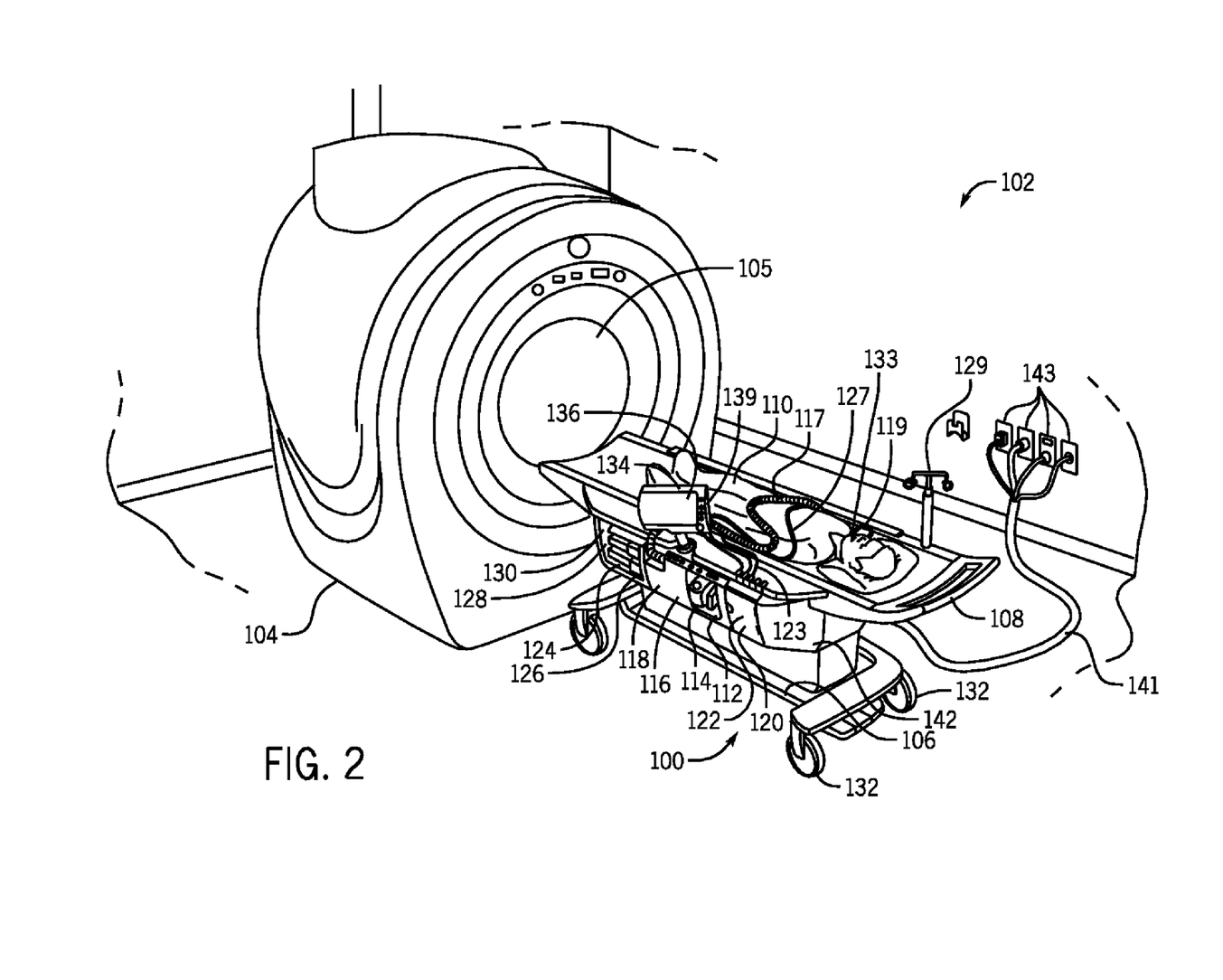
FIG. 2 is a pictorial view of a patient transport apparatus and an MRI system magnet according to an embodiment of the invention.

FIG. 2 shows a pictorial view of a mobile patient transport apparatus 100 according to an embodiment of the present invention. Transport apparatus 100 is shown positioned in an MR examination room 102 of a healthcare facility such as, for example, a hospital or clinic. The MR examination room 102 includes an MR imaging system magnet 104, such as magnet assembly 52 of FIG. 1. Transport apparatus 100 includes a base 106 and a table 108 to support a patient 110, who may be anesthetized before or after entering MR examination room 102. Base 106 has a plurality of bays or compartments configured to house a plurality of patient care modules. The plurality of bays include, for example, a bay 112 for an anesthesia gas mixing module 114 (also shown in FIG. 9), a bay 116 for a ventilator module 118 (also shown in FIG. 9), a bay 120 for a patient monitoring module 122 (also shown in FIG. 9), a bay 124 for an intravenous (IV) pump module 126, and a bay 128 for an injector module 130. A plurality of wheels 132 are attached to base 106 to allow transport apparatus 100 to be pushed and rolled to and from MR examination room 102.

A video display module 134 is attached to base 106 and is connected to a controller 138 (discussed below with respect to FIG. 9), which can be configured to communicate with and control the plurality of patient care modules. Video display module 134 includes a video panel 136 configured to display patient care parameters and other outputs of the plurality of patient care modules positioned on or within transport apparatus 100 as well as their various functions and options available for selection and control. In an embodiment of the invention, video panel 136 is a touch screen allowing medical personnel to select and manipulate objects on video panel 136 to send user inputs to the controller 138 for control of the plurality of patient care modules. In another embodiment, a plurality of buttons 139 allows medical personnel to select and manipulate objects on video panel 136 to control the plurality of patient care modules. Additionally, each patient care module may have various buttons and control means to facilitate individual operation of the module.

A ventilator module (also shown in FIG. 9) 118 insertable into bay 116 typically includes support hardware such as a breathing tube 117 and a face mask 119 used to both provide anesthesia and life support gases to the patient and to facilitate respiration. According to an embodiment of the invention, ventilator module 118 may include an endotracheal tube to deliver anesthesia and life support gases to the patient. The ventilator module 118 is configured to perform the breathing function for anesthetized patients. The ventilator module 118 is controlled by a controller 138 or computer in an embodiment of the invention to allow delivery of specific flow rates of gases based on operator-specified settings. The gases may include air or anesthetic agents. The ventilator module 118 may be driven pneumatically or may use a diaphragm pump or a turbine to generate gas flow. A breathing system of the ventilator module 118 typically includes flow sensors, filters, check valves, pressure relief valves, breathing tubes (such as breathing tube 117), and various other electromechanical components to accurately and safely deliver the correct volume and pressure of gas to the patient. Computer control of the ventilator module 118 allows accurate delivery of a specific volume, a specific pressure, or some combination of the two at a specified rate. It is contemplated that ventilator module 118 may be configured to sense if the patient is trying to breathe and to support those efforts if possible.

Embodiments of the ventilator module 118 include those with circle systems that scrub the carbon dioxide exhaled by the patient and recycle the gas/anesthetic agent. Other embodiments employ an open system that does not recycle the gas/anesthetic agent. However, both recycling system types typically use a scavenging system to remove expired gases/anesthetic agents from the breathing system and into a containment system of the healthcare facility. In another embodiment, ventilator module 118 includes a circle system with a carbon filter, thereby eliminating the need for a scavenging system. Ventilator module 118 also includes a bag to facilitate manual ventilation and a suction device to clear out a patient airway.

Anesthesia module 114 typically works in conjunction with the ventilator module 118. In an embodiment of the invention, anesthesia module 114 includes a vaporizer (not shown) to vaporize the anesthetic agent and a gas mixer (not shown) to mix the anesthetic agent with carrier gases. The gas mixer is preferably computer-controlled to mix agent and carrier gases based on user-supplied settings and can be driven using pneumatic and/or electric power. The specified anesthetic agent/carrier gas mixture is routed from the gas mixer to the ventilator module 118 for delivery to the patient. In operation, the anesthesia module 114 may receive the anesthetic agent and carrier gases from a source external to the patient transport apparatus 100 during the MRI scan procedure. However, as described below with respect to FIG. 3, anesthetic agent and carrier gases may be on board the transport apparatus 100.

A patient monitoring module 122 (also shown in FIG. 9) insertable into bay 120 may be used to measure various physiological vital functions of the patient including, but not limited to: blood pressure, heart rate, temperature, and oxygen saturation. Patient monitoring module 122 may also be configured to monitor the depth of anesthesia. Subsystems of the patient monitoring module configured to measure and/or collect patient physiological vital function data typically gather such data through electrical wires and/or pneumatic lines, generally designated 123, which run from the monitoring module 122 to the patient. These wires and lines may be taped, clipped, or wrapped around the patient. In the case of temperature or blood pressure, sensors (not shown) may be inserted in the patient for invasive monitoring thereof. Patient physiological vital function data collected by monitoring module 122 may be viewed in real-time locally on video display panel 136 or remotely (e.g., in the MRI control room).

The patient monitoring module 122 may also be configured to monitor patient gases to measure, for example, the concentrations of different gases inhaled or exhaled by the patient. The patient monitoring module 122 typically includes gas sample lines 133 connected at various locations within the ventilator module 118 breathing system.

One embodiment of an IV pump module 126 (also shown in FIG. 9) insertable into bay 124 includes a peristaltic mechanical delivery system and a user interface for setting a flow rate for intravenous fluids. IV pump module 126 is configured to continuously deliver a specified amount of an IV drug or fluid based on the user settings. The pump module 126 includes at least one IV line 127 running from the IV pump module 126 to the patient for carrying the IV fluids to the patient. An embodiment of the IV pump module 126 incorporates a computer modeling feature to help predict the effect of a certain dose of a drug on a specific patient. An IV support post 129 attached to base 106 may be used to route IV line 127 to the patient or may be used to hold IV fluid bags or pouches as needed. In some instances, patients may be anesthetized using only IV anesthesia. If the patient does not need to be deeply anesthetized and can breathe on his own, a total IV anesthesia (TIVA) may be administered. In such cases, the anesthesia and ventilator modules might not be used.

One embodiment of an injector module 130 (also shown in FIG. 9) insertable into bay 128 includes an IV line (not shown) used to deliver MRI contrast agents to the patient. The injector module usually operates at a higher flow rate and for a shorter period of time than the IV pump module 126. An embodiment of the injector module 130 includes a delivery unit (not shown) and a control unit (not shown). The delivery unit generally includes a piston-based mechanism and two containers for the delivery and flushing of a contrast agent. The control unit is typically placed at or near the MR technical work area and generally includes a user interface (not shown) and display unit (not shown) that enables the technician to program and execute the injection of a contrast agent in conjunction with the MR scanning procedure.

Transport apparatus 100 includes a battery compartment 142 to hold one or more batteries (shown in FIG. 9) to power the patient care modules when transport apparatus 100 is not connected to an external power supply. For example, when the patient is transported from an area of the healthcare facility, such as the intensive care unit (ICU), to the MR examination room 102, the batteries provide power to keep the plurality of patient care modules positioned on or within transport apparatus 100 powered and functioning. In an embodiment of the invention, compartment 142 has a plurality of battery slots (not shown) for hot swapping of batteries. In yet another embodiment of the invention, transport apparatus 100 includes compartment 142 to hold one or more fuel cells to power the patient care modules when transport apparatus 100 is not connected to an external power supply.

In an embodiment of the invention, the patient care modules positioned on or within transport apparatus 100 are MRI-compatible. That is, it is desired that the patient care modules have no more than an acceptable amount of ferromagnetic material for use in and around an MRI system. Preferably, the patient care modules have no amount of ferromagnetic material. It is further desired and contemplated that the patient transport apparatus 100 and the patient care modules include appropriate shielding (not shown) for any ferromagnetic material that does exist therein.

Because patient transport apparatus 100 integrates various patient control modules that would otherwise have to be positioned, and operated, separately as free-standing medical devices about the patient 110, healthcare professionals are able to process MRI patients 110 more quickly through the scanning process using the transport apparatus 100. Patient throughput increases due to reduced setup time, that is, the patient modules can be setup and activated before patient 110 enters the MRI examination room 102. The patient care modules can be attached and activated immediately after the patient 110 is transferred to the patient transport apparatus 100. Furthermore, safety is improved by eliminating many of the cables that would have to be routed between separate, non-integrated free standing medical devices and the patient. The patient transport apparatus 100 includes a control system 138 (shown in FIG. 9) that allows centralized, and even remote, control of the patient care modules thereby eliminating the need for extra medical personnel. One or two operators in the MRI control room could conceivably monitor and control the patient modules and carry out the MR scanning process.

Figures 3, 4, 5, 6, 7:
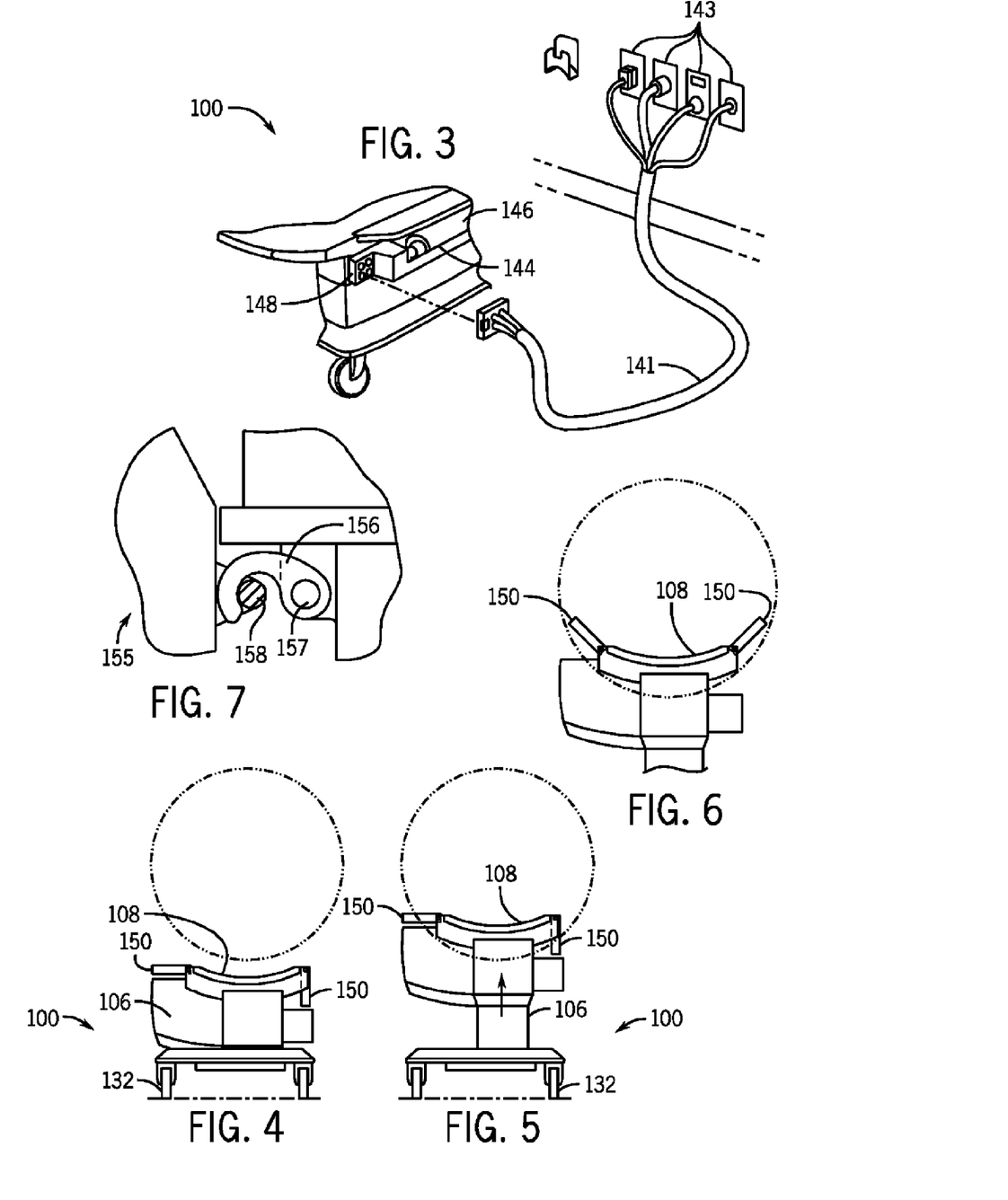
FIG. 3 is a pictorial view of a cable connected at one end to a connection port on the patient transport apparatus, and at the other end to a stationary outlet.
FIG. 4 is a side view of the patient transport apparatus showing the table height adjusted to a low position.
FIG. 5 is a side view of the patient transport apparatus showing the table height adjusted to a high position.
FIG. 6 is a side view of the patient transport apparatus showing the arm tables angled upward.
FIG. 7 is a side view of a docking mechanism which connects the patient transport apparatus to an MR system magnet.

FIG. 3 illustrates a pictorial view of a portion of the side of transport apparatus 100 opposite the side shown in FIG. 2. A compartment 144 on transport apparatus 100 is configured to receive one or more containers or tanks 146 for the storage and supply of life support gases to respective patient care modules. For example, one or more tanks 146 may store and supply oxygen to patient 110 (shown in FIG. 2) or store and supply an anesthetic agent and carrier gas to anesthesia module 114 (shown in FIG. 2).

A connection port 148 on transport apparatus 100 is provided to allow transport apparatus 100 to be coupled via a tether or cable 141 (also shown in FIG. 2) to a plurality of stationary wall outlets 143 (also shown in FIG. 2). Cable 141 includes respective couplers and media for connecting to and transporting electrical power, communications, and medical gases to transport apparatus 100 from external sources (not shown). In this manner, transport apparatus 100 and any patient care modules positioned therein may be supplied with the functions needed for operation to support or substitute the functions on board transport apparatus 100. Communication media in cable 141 allow for the control of transport apparatus 100 and any patient care modules positioned therein from an external location such as an adjacent control room (not shown) or other location in the healthcare facility. It is also contemplated that the external location may be at a location remote from the healthcare facility.

Returning to FIG. 2, to facilitate alignment of the patient with magnet 104, a portion of base 106 is height-adjustable so that table 108 may be aligned with a bore 105 of magnet 104. FIG. 4 shows an end view of transport apparatus 100 with base 106 adjusted such that table 108 is at a low-height position. As discussed below, table 108 is insertable into bore 105 (shown in FIG. 2). Accordingly, FIG. 5 shows an end view of transport apparatus 100 with base 106 adjusted such that table 108 is at a higher height for aligning table 108 with bore 105 (shown in FIG. 2). In one embodiment of the invention, base 106 incorporates a hydraulic lift mechanism (not shown) to enable height adjustment. It is contemplated that a pneumatic or manual apparatus may be also be used for height adjustment. Wheels 132 (also shown in FIG. 4) allow for axially positioning transport apparatus 100 with the bore.

A pair of adjustable arm tables 150 (also shown in FIG. 4) is pivotally attached to table 108 and may be set in a horizontal position to support the patients' arm during insertion of an IV line into the patient. Arm tables 150 may be set in a vertical downward position to facilitate access to the patient. For positioning table 108 within bore 105 (shown in FIG. 2), FIG. 6 shows a positioning of arm tables 150 at an angle higher than horizontal to both position arm tables 150 within a volume of the bore and to help cradle the patient during extension and retraction of table 108.

FIG. 7 shows a partial side view of a docking system 155 for securely coupling transport table 100 (shown in FIG. 2) to a magnet (for example, magnet 104 shown in FIG. 2) according to an embodiment of the invention. A latch hook 156 rotates on a pivot 157 attached to base 106 (shown in FIG. 2). Latch hook 156 engages a pin 158 attached to the magnet to couple and dock transport apparatus to the magnet.

Figure 8:
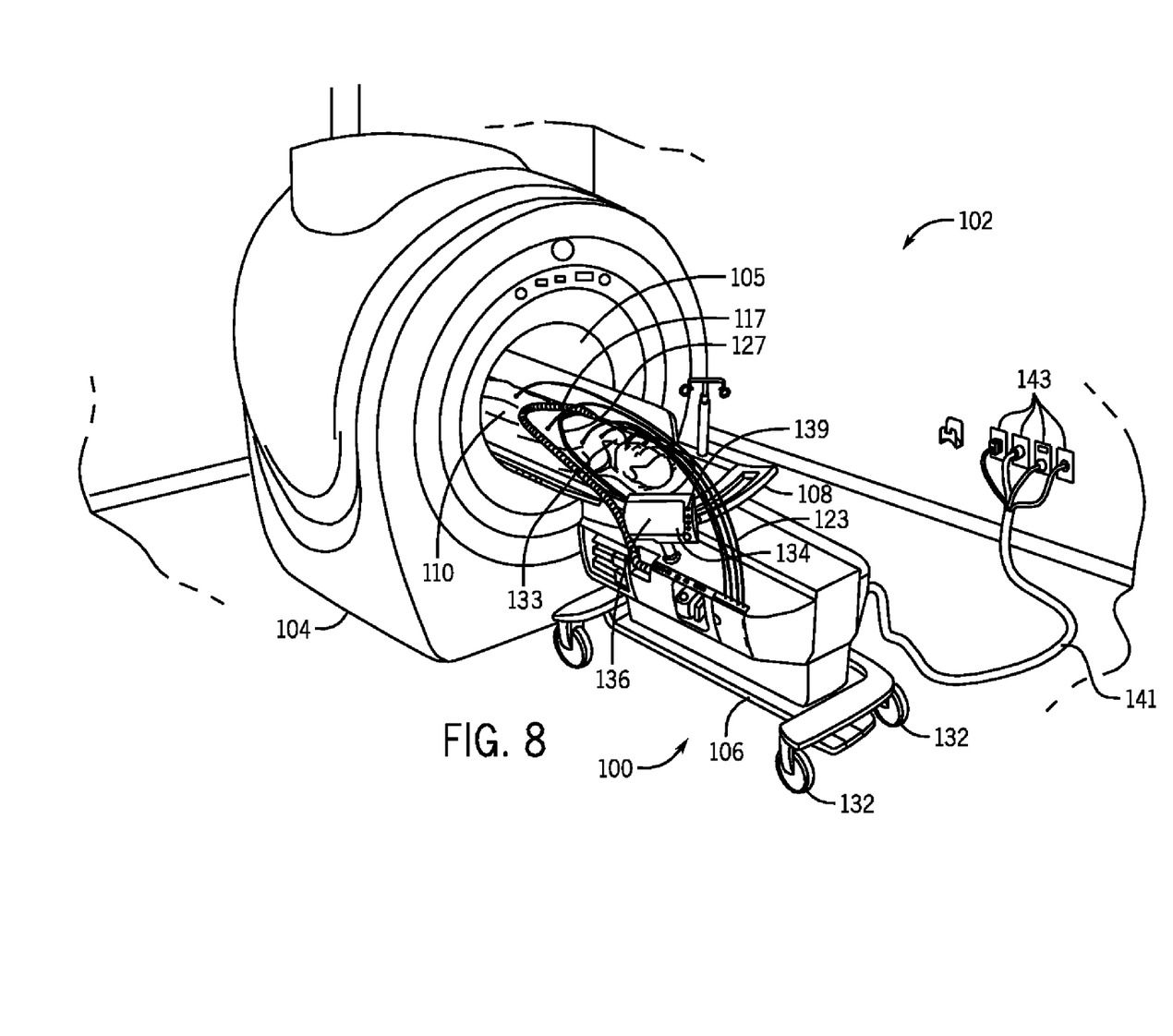
FIG. 8 is a pictorial view of an MRI system magnet and a patient transport apparatus showing a table detaching from a base to transfer a patient into the magnet.

FIG. 8 illustrates a pictorial view of a table at least partially inserted into a bore for scanning the patient according to an embodiment of the invention. As shown, table 108 is configured to be detachable from base 106. In this manner, table 108 allows a patient 110 (e.g., an anesthetized patient) to be transferred into bore 105 for an MRI scan without having to move the patient 110 from one table to another. Breathing tube 117, IV line 127 and patient monitoring cables 123 move with patient 110 into MRI magnet 104 and are of sufficient length to allow patient 110 to be fully inserted into bore 105. Accordingly, an anesthetized patient 110 may be kept in an anesthetized state during the scanning procedure. Furthermore, table 108 may contain an array of RF coils (not shown) to receive MR signals used to reconstruct an image.

Figure 9:
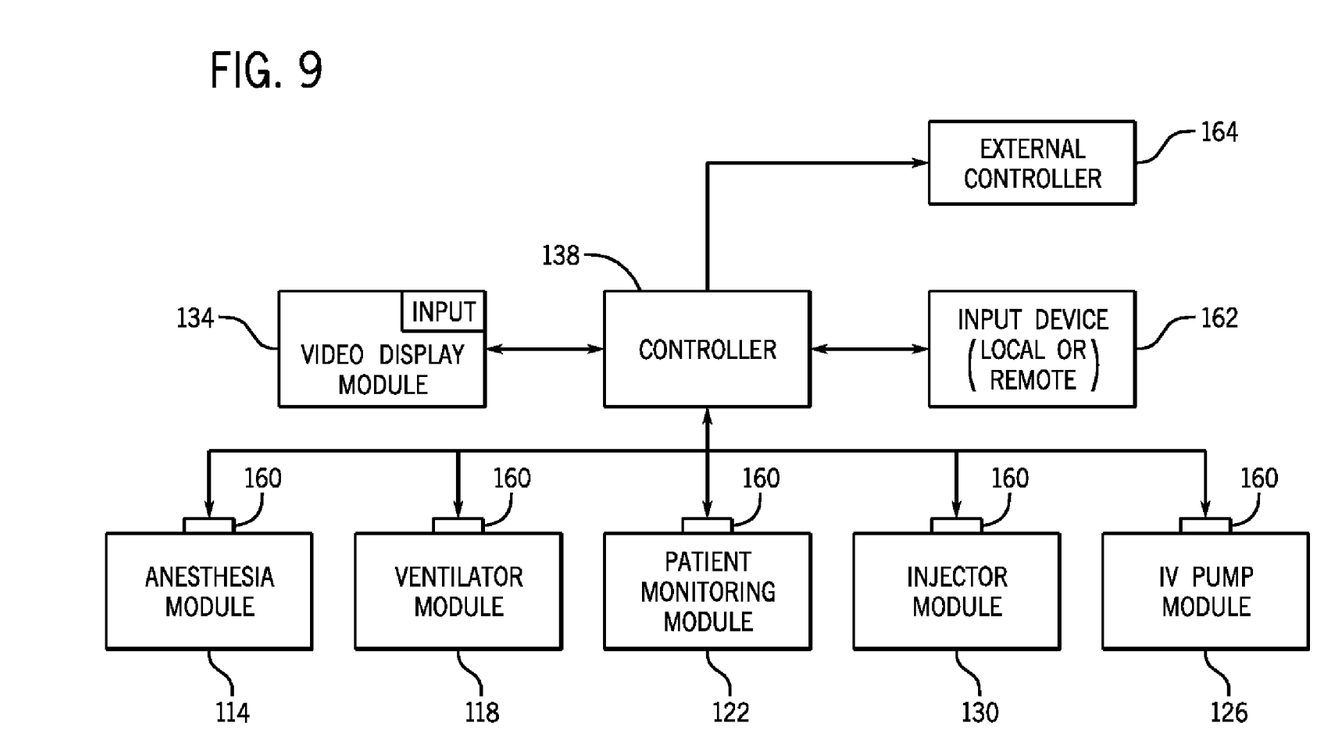
FIG. 9 is a block diagram depicting the relationship of the patient care modules to a controller, input device and display apparatus.

FIG. 9 is a block diagram depicting the relationship of the patient care modules to a controller, input device and display apparatus. A controller 138 is connectable to a plurality of patient care modules for control thereof and communication therewith. In an embodiment of the invention, the plurality of patient care modules include an anesthesia module 114, a ventilator module 118, a patient monitoring module 122, an injector module 130, and IV pump module 126, as described above. Each patient care module has a connector 160 to electrically couple the respective patient care module to controller 138. A respective mating connector (not shown) for each of the connectors 160 is positioned in a corresponding bay 112, 116, 120, 124, 128 (shown in FIG. 2) according to an embodiment of the invention. Controller 138 is programmed to control and communicate with each of the patient care modules positioned on transport apparatus 100 (shown in FIG. 2). A user input device 162, such as a keyboard, may be integrated with base 106 (shown in FIG. 2) of transport apparatus 100 to send user commands to controller 138. As described above with respect to FIG. 2, video display module 134 may also send user commands to controller 138. Additionally, an external controller 164 may be coupled to controller 138 through cable 141 (shown in FIGS. 2 and 3). In this manner, controller 138 may be programmed to perform in a slave mode and to relay commands and communications between external controller 164 and patient care modules 114, 118, 122, 126, 130. External controller 164 may be, for example, in an adjacent control room or other location in a healthcare facility or may be at a location remote from the healthcare facility.

In an embodiment of the invention, a patient transport apparatus having a table configured to support a patient, a base attached to the table, a docking system attached to the base, the docking system configured to couple to a mating docking system of an MR imaging system, and a plurality of bays formed in the base, with each bay configured to receive a patient care module therein. The patient transport apparatus further includes a control system configured to be electrically coupled to each patient care module received within the plurality of bays and configured to centrally control each patient care module.

According to another embodiment of the invention, a patient imaging system including a magnetic resonance imaging (MRI) system having a plurality of gradient coils positioned about a bore of a magnet, and an RF transceiver system and an RF switch controlled by a pulse module to transmit RF signals to an RF coil assembly to acquire MR images. The patient imaging system further includes a plurality of patient care modules configured to provide patient care during an imaging session and a patient transport apparatus, wherein the transport apparatus comprises a table configured to support a patient and a base attached to the table. The base includes a plurality of compartments having the plurality of modules positioned therein, a controller configured to control each of the plurality of modules, and a docking system configured to removeably attach the patient transport apparatus to the MRI system.

In yet another embodiment of the invention, a method of manufacturing a patient transport apparatus that includes coupling a table for supporting a patient to a base, forming a plurality of compartments in the base capable of accepting a plurality of patient care modules therein, attaching a docking mechanism to the base, wherein the docking mechanism is capable of coupling the patient transport apparatus to an MRI system magnet, and providing a controller capable of controlling each of the plurality of patient care modules.

While transport apparatus 100 has been described with respect to its use in MR imaging, one skilled in the art will recognize that embodiments of the apparatus can be utilized in other areas including, but not limited to, intensive care and critical care units, operating rooms, or in examinations where it is advantageous to have the patient anesthetized.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A patient transport apparatus comprising:
    a table configured to support a patient;
    a base attached to the table;
    a docking system attached to the base, the docking system configured to couple to a mating docking system of an MR imaging system;
    a plurality of bays formed in the base, each bay configured to receive a patient care module therein and magnetically shield the patient care module from a magnetic field generated by the MR imaging system; and
    a control system configured to be electrically coupled to each patient care module received within the plurality of bays and configured to centrally control each patient care module;
    wherein the table is detachable from the base and configured to be transferred into a bore of an MRI system magnet to enable an acquisition of MR images of the patient, such that the patient care modules received in the plurality of bays in the base are kept outside of the bore of the MRI system during the acquisition of MR images.

2. The patient transport apparatus of claim 1 wherein the plurality of bays comprises:
    a first bay configured to receive an anesthesia module, the anesthesia module configured to combine an anesthetic agent with a carrier gas;
    a second bay configured to receive a ventilator module, the ventilator module configured to deliver gases to the patient via a breathing tube; and
    a third bay configured to receive a patient monitoring module, the patient monitoring module configured to collect medical data from the patient and transmit the collected medical data to the control system.

3. The patient transport apparatus of claim 2 wherein the plurality of bays further comprises a fourth bay configured to receive one of an intravenous (IV) pump module configured to provide fluids intravenously to the patient and an injector module configured to provide an MRI contrast agent to the patient.

4. The patient transport apparatus of claim 1 further comprising a video display module configured to display patient data and patient care module systems data.

5. The patient transport apparatus of claim 4 wherein the control system comprises a user input device integrated with one of the video display module and the base.

6. The patient transport apparatus of claim 1 further comprising a compartment configured to store a container for life support gases.

7. The patient transport apparatus of claim 1 further comprising a compartment configured to house one of a battery and a fuel cell configured to provide power to a patient care module.

8. The patient transport apparatus of claim 1 further comprising a connection port configured to receive one of electrical power, patient gases, and electronic communications from a source external to the patient transport apparatus.

9. The patient transport apparatus of claim 1 wherein the base is configured to permit adjustment to a height of the table.

10. A patient imaging system comprising:
    a magnetic resonance imaging (MRI) system having a plurality of gradient coils positioned about a bore of a magnet, and an RF transceiver system and an RF switch controlled by a pulse module to transmit RF signals to an RF coil assembly to acquire MR images;
    an anesthesia system comprising a plurality of patient care modules configured to anesthetize and monitor a patient during an MR imaging session; and
    a patient transport apparatus comprising:

a table configured to support a patient; and
a base attached to the table, the base comprising:
- a plurality of compartments having the plurality of modules positioned therein;
- a controller configured to control each of the plurality of modules; and
- a docking system configured to removeably attach the patient transport apparatus to the MRI system;

wherein the table is detachable from the base and configured to be transferred into the bore to enable acquisition of MR images during the MR imaging session, such that the anesthesia system positioned in the plurality of bays of the base are kept outside of the bore during the MR imaging session.

11. The patient imaging system of claim 10 wherein the plurality of patient care modules comprises an anesthesia module, a ventilator module, and a patient monitoring module.

12. The patient imaging system of claim 11 wherein the plurality of patient care modules further comprises one of an intravenous (IV) pump module and a contrast agent injector module.

13. The patient imaging system of claim 10 further comprising a video display module configured to display real-time patient and systems data.

14. The patient imaging system of claim 10 wherein the patient transport apparatus further comprises an external connector port configured to receive electrical power, patient gases, and electronic communications from a source external to the patient transport apparatus.

15. The patient imaging system of claim 10 wherein each of the plurality of compartments is configured to magnetically shield the patient care module from a magnetic field generated by the MRI system.

16. A method of manufacturing a patient transport apparatus comprising:
coupling a table for supporting a patient to a base;
forming a plurality of compartments in the base capable of accepting a plurality of patient care modules therein, the plurality of compartments configured to magnetically shield the plurality of patient care modules to enable positioning of the plurality of patient care modules in proximity to an MRI system magnet;
attaching a docking mechanism to the base, wherein the docking mechanism is capable of coupling the patient transport apparatus to the MRI system magnet; and
providing a controller capable of controlling each of the plurality of patient care modules;
wherein coupling the table to the base comprises detachably coupling the table to the base, such that the table can be translated into a bore of the MRI system magnet to acquire MR images of the patient while the base, and the plurality of patient care modules positioned in the plurality of compartments in the base, are kept outside of the bore of the MRI system magnet during acquisition of the MR images.

17. The method of claim 16 further comprising assembling one of an anesthesia module, a ventilator module, and an IV pump module into one of the plurality of compartments.

18. The method of claim 16 further comprising assembling a connector port to the base, the connector port configured to receive, from a source external to the patient transport apparatus, one of electrical power, patient gases, and electronic communications.

19. The method of claim 16 further comprising forming a compartment in the base capable of accepting a life support gas container therein.

* * * * *